United States Patent [19]

Marcus

[11] Patent Number: 4,553,837
[45] Date of Patent: Nov. 19, 1985

[54] ROLL FINGERPRINT PROCESSING APPARATUS

[75] Inventor: Daniel H. Marcus, New City, N.Y.

[73] Assignee: Fingermatrix, Inc., North White Plains, N.Y.

[21] Appl. No.: 544,956

[22] Filed: Oct. 24, 1983

[51] Int. Cl.$^4$ ............................ G06K 9/00; G06K 9/20
[52] U.S. Cl. ........................................................ 356/71
[58] Field of Search ............................ 356/71; 382/4, 5

[56] References Cited

U.S. PATENT DOCUMENTS 4,322,163  3/1982  Schiller ................................. 356/71

Primary Examiner—Vincent P. McGraw
Attorney, Agent, or Firm—McAulay, Fields, Fisher, Goldstein & Nissen

[57] ABSTRACT

A fingerprint processing apparatus is capable of generating a roll fingerprint image on a flat plane without distorting the image of the fingerprint. The apparatus includes a source of an interrogating light beam, optical scanning equipment, an array of photoelectric transducers, lenses, and electrical scanning equipment. A cylindrical-segment platen is provided having an upper surface with an anti-reflective coating which receives, positions and supports a finger, and a lower surface which receives and transmits the interrogating light beam. A finger positioned on the upper platen surface modulates the interrogating light beam to provide a reflected light beam having fingerprint information. A motor rotates the light source, optical scanning equipment, array, lenses, and an element of the electrical scanning equipment. The axis of rotation of the optical scanning equipment is substantially the same as the axis of the upper surface of the platen. The optical scanning equipment scans the circumference of the platen such that the angle of incidence of the light beam on the fingerprint object at the curved back of the platen remains constant. The electrical scan is along the axis of the platen. The array receives the modulated light beam and converts the fingerprint information into sets of information signals. The electrical scanning means scans the information signals and synchronizes the electrical scan to incremental positions of the optical scan.

10 Claims, 4 Drawing Figures

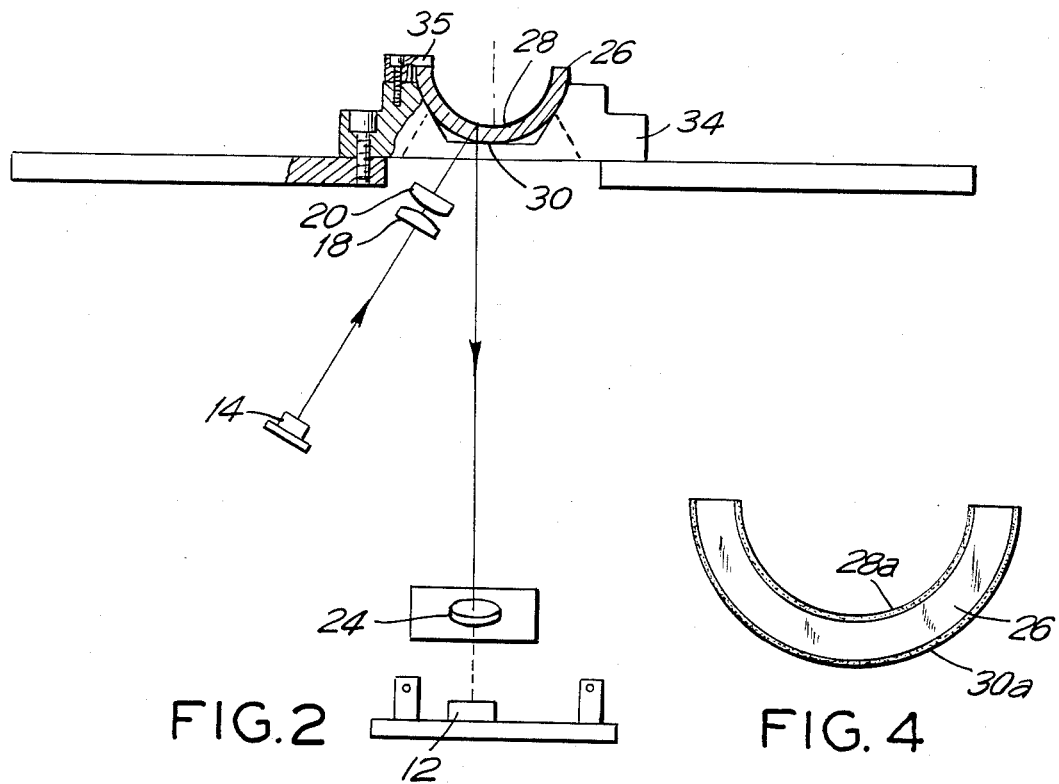
FIG. 2
FIG. 4
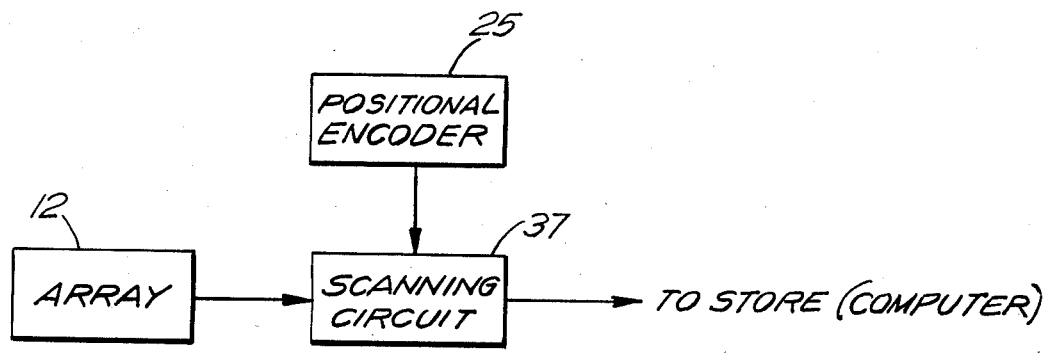
FIG. 3

ROLL FINGERPRINT PROCESSING APPARATUS

BACKGROUND OF THE INVENTION

This invention relates generally to a fingerprint processing apparatus and more particularly to a fingerprint processing apparatus capable of generating a roll fingerprint image.

Fingerprint processing apparatus capable of generating a fingerprint image which can be encoded into machine readable signals are known in the art. Examples of such apparatus are described in issued U.S. Pat. No. 4,322,163 and in co-pending application Ser. No. 472,640 filed on Mar. 7, 1983 which is a continuation in part of application Ser. No. 210,174 filed on Nov. 11, 1980. U.S. Pat. No. 4,322,163 and application Ser. No. 472,640 are incorporated herein by reference. These apparatus generate a flat touch fingerprint image using an interrogating light beam which is displaced across a flat platen having a finger supported thereon. The finger on the platen modulates the interrogating light beam to provide a reflected light beam having fingerprint information. Optical scanning means are used which are capable of causing the interrogating light beam to scan the fingerprint object created by the finger on the platen. The modulated light beam is imaged onto an array of photo-electric transducers to provide a series of output signals indicative of the modulated information. The output of the array is serially interrogated at successive scan positions to provide a set of signals containing the fingerprint image.

This type of apparatus is primarily used in access control systems to quickly, accurately, and inexpensively verify the fingerprints of known individuals, by electronically matching the subject's fingerprint pattern to those in a previously obtained file stored in a computer memory.

These known fingerprint processing apparatus operate on a flat fingerprint object on a flat plane. The flat nature of the object being scanned permits use of a relatively simple, inexpensive optical scan system.

When using fingerprint processing apparatus of this type, proper positioning of the finger on the platen is important. In order to obtain repeatable, identifiable fingerprint images, the finger must be placed on approximately the same position on the platen each time a scan is made.

In law enforcement, where fingerprints are frequently utilized to identify unknowns, a roll fingerprint image known as a Henry roll is used. The Henry roll fingerprint by nature includes considerably more information than is contained on a flat touch fingerprint since it is wider and provides a full core and delta picture. Henry roll fingerprints, stored on print cards, are generated by conventional methods such as taking ink impressions from individual fingers. These conventional methods have many disadvantages; they are messy and they do not consistently provide an accurate fingerprint image.

Accordingly, it is a purpose of this invention to provide a fingerprint processing apparatus capable of generating an improved roll fingerprint image which is compatible with existing Henry roll fingerprint images.

It is another object of this invention to provide an apparatus which generates a roll fingerprint image without distorting the image of the fingerprint.

It is a further object of this invention to provide such an apparatus whereby an accurate and unambiguous roll fingerprint image can be generated by relatively easy to use and relatively inexpensive equipment.

It is further the object of the invention, to provide a fingerprint processing apparatus which is comfortable to use and which aids in properly positioning the finger being scanned.

A further object of this invention is to provide a fingerprint processing apparatus which is usable for law enforcement identification purposes, by capturing a roll fingerprint image which may be directly compared with existing inked card rolled fingerprints stored in law enforcement agency files, either by manual search or computer search techniques.

Yet another object is to provide such an apparatus which generates a roll fingerprint image without the use of inks.

BRIEF DESCRIPTION

In one embodiment of the invention, an improved fingerprint processing apparatus is provided which is capable of generating a roll fingerprint image. The improved fingerprint processing apparatus includes a source of an interrogating light beam. The interrogating light beam is modulated by the ridge and valley zones of the fingerprint to provide a reflected light beam having fingerprint information. Optical scanning means are provided which are capable of causing the interrogating light beam to scan a fingerprint object. An array of photo-electric transducers is provided. An optical lens positioned in the path of the reflected light produces a fingerprint image at the array. The array is arranged in a predetermined linear form to receive the modulated light beam and to convert the fingerprint information carried by the modulated light beam into a plurality of sets of information signals representing a line by line scan of the fingerprint object. Electrical scanning means are provided to electrically scan the information signal output of the array and to synchronize the electric scan to incremental positions of the optical scanning beams.

In the improved fingerprint processing apparatus of this invention the platen is a cylindrical-segment platen. When a finger is pressed against the platen a fingerprint object having ridge zones and valley zones is provided at the upper surface of the platen. The platen has an upper surface which receives, supports and positions a finger. The platen has a lower surface which receives and transmits the interrogating light beam. The upper platen surface has a thin anti-reflective coating to provide image enhancement on the surface. The lower platen surface has a similar anti-reflective coating to remove unwanted background light in the modulated signal. The interrogating light beam is collimated and shaped to scan the width of the finger positioned on the platen.

The light source, scanning means, array, and lens are all mounted for coordinated rotary movement. The rotary movement is such that axis of rotation of the optical scanning means is the same as the axis of the upper surface of the cylindrical segment platen.

The optical scanning means scans the circumference of the platen. Because of the rotation of the scanning means the angle of incidence of the light beam on the fingerprint object at the curved back surface of the platen remains constant. The electrical scan is along the axis of the cylindrical platen. The apparatus generates a roll fingerprint which is compatible with existing Henry roll fingerprints.

BRIEF DESCRIPTION OF THE DRAWINGS

FIG. 2 is an optical and mechanical schematic drawing of the FIG. 1 roll fingerprint apparatus.

FIG. 3 is a block diagram illustrating the arrangement for electronically scanning the optical image to provide a two dimensional set of pixel values representing the fingerprint image.

FIG. 4 is an enlarged, exploded, sectional view of the cylindrical segment platen of the FIG. 1 roll fingerprint apparatus.

DESCRIPTION OF THE PREFERRED EMBODIMENTS

Figure 1:
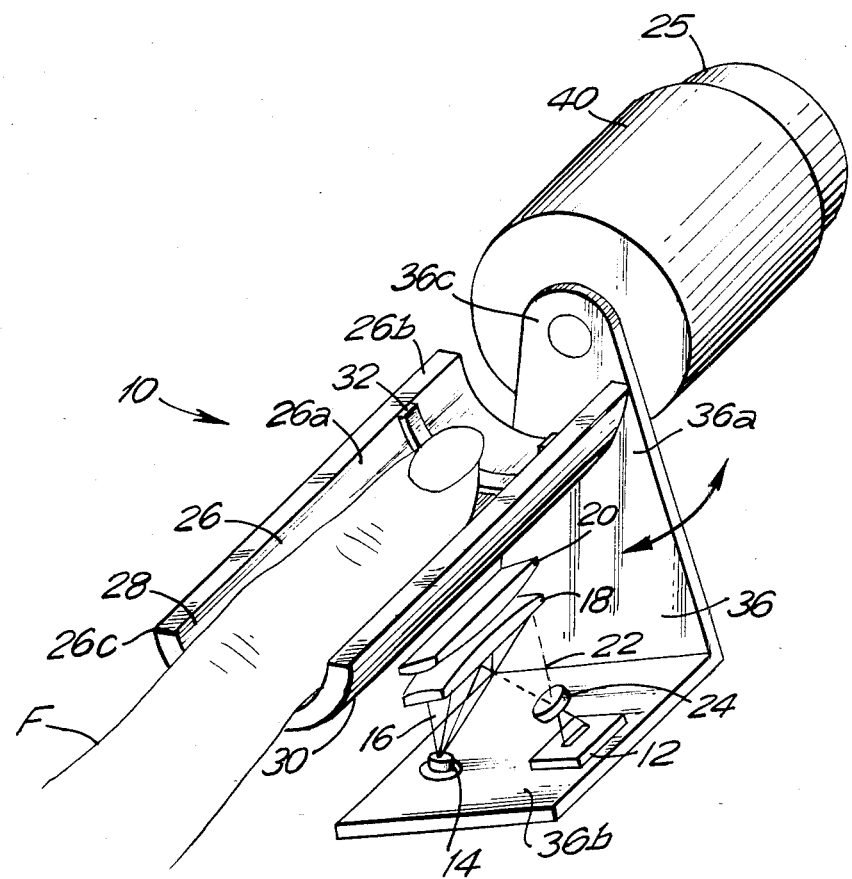
FIG. 1 is a perspective view of an embodiment of the roll fingerprint processing apparatus of the present invention.

Referring now to the drawings, the reference numeral 10 denotes the roll fingerprint processing apparatus. The apparatus includes a linear photodiode array 12. The photodiode array is conventional in construction and may, for example, comprise photodiode array Model No. CCD 133 manufactured by the Fairchild Semiconductor Division of Fairchild Camera & Instrument Co., of Mountainview, Calif. This particular array comprises 1,024 photodiodes that extend in the longitudinal direction. The diodes are aligned in contact with one another and each diode is about 0.02 mm. on a side. Accordingly, the shape of the light receiving opening of the array is in the form of a slit wherein the long dimension of the slit corresponds to the longitudinal direction of the array.

A solid state laser 14 is used as a source of an interrogating light beam 16. Laser 14 provides a beam of collimated light. As used herein collimated light refers to a light beam in which the rays do not scatter. It is not essential that the light rays be parallel to one another. It is only essential that they do not crossover one another. Thus, a collimated light beam may be diverging, parallel or converging.

Spherical condensing lenses 18 and 20 are positioned in the path of interrogating light beam 16 to concentrate the light beam so that adequate light intensity is provided at the object fingerprint, and to shape the illuminating rays into a cone whose vertex is approximately at the aperture of the imaging lense 24.

Interrogating light beam 16 can be modulated so that it contains fingerprint information. The modulation of light beam 16 will be explained in full hereinafter. After light beam 16 is modulated, it is referred to as reflected light beam 22. Reflected light beam 22 contains fingerprint information. An imaging lens 24 is provided which projects the fingerprint image from reflected light beam 22 onto array 12. The fingerprint image projected onto array 12 contains light and dark spots indicative of the fingerprint information.

A positional encoder 25 produces a signal for each predetermined incremental angular advancement of the optical system. This signal is applied to scanning circuit 37 which interrogates array 12 in response to each signal. Scanning circuit 37 provides an output signal each time array 12 is interrogated. The output signal is representative of the fingerprint information at each position where the array is interrogated.

Elements of this scanning apparatus are conventional and are similar to those described in issued U.S. Pat. No. 4,322,163.

System 10 uses a cylindrical-segment platen 26. Platen 26 has an upper platen surface 28 which is shaped and dimensioned to receive, support and position a finger F. Platen 26 has a lower platen surface 30 which is adapted to receive interrogating light beam 16. Preferably both upper surface 28 and lower surface 30 have a thin anti-reflective coating 28a and 30a. The anti-reflective coatings reduce the magnitude of reflection at the interface between the air and the platen 26.

Platen 26 is longer than the length of that portion of finger F to be scanned. Finger F is positioned on platen 26 using a stop 32 with the portion of finger F to be scanned lying on a central platen segment 26a. A platen holder 34 supports the platen 26 and is connected to forward platen segment 26b and rear platen segment 26c using clamps 35 or other appropriate means.

A rotating L-shaped bracket 36 having a leg portion 36a and a platform portion 36b supports condensing lenses 18 and 20, imaging lens 24, array 12, and laser 14. Rotating bracket 36 is connected, at its top end 36c to a rotary motor 40. The positional encoder 25 is coupled to motor 40. Thus motor 40 can rotate condensing lenses 18 and 20, imaging lens 24, array 12, laser 14 and positional encoder 25 so that the finger F on platen 26 may be scanned. Finger F on platen 26 when scanned modulates light beam 16 so that it provides a fingerprint image having ridge zones and valley zones. The rotation is such that the axis of rotation of the optical scan is the same as the axis of the upper surface of the platen 26.

Platen 26 provides a surface for finger contact which is about 180°. The rotation of the optical scanning means causes the angle of incidence of the interrogating light beam on the fingerprint object at the back surface of the platen to remain constant. For mechanical design convenience, the angle of incidence is about 8°. The optical scanning means scans the circumference of platen 26, along an arc of about at least 150° and preferably along an arc of 180°. The electrical scan is along the cylindrical axis of platen 26. The scans provide a nail edge to nail edge picture which is equivalent to a Henry roll fingerprint.

The curved surface of platen 26 causes the reflected light to diverge in one axis, but the lens aperture is large enough to accomodate this divergence.

In operation the finger F is placed on upper platen surface 26. The laser 14 produces interrogating light beam 16 which impinges on the finger F pressed on platen 26. This light is modulated and reflected as reflected light beam 22 to the diode array 12. The positional encoder 25 produces a synchronizing signal at angular intervals corresponding to the linear separation between successive optical scan lines. This signal tells the scanning circuit 37 to interrogate array 12 at precise locations and to provide output signals representing the fingerprint information at each cell of array 12. The interrogation of array 12 is determined by positional encoder 25 and is not dependent upon the speed of the rotary movement. The procedure of interrogating array 12 and providing output signals is continued until the entire fingerprint object has been scanned.

Motor 40 is energized and as motor 40 moves, the positional encoder 25, the bracket 36, and all of the apparatus elements mounted upon bracket 36 simultaneously rotate.

Preferably, a number of differently sized platens, all substantially similar to platen 26, are provided so that differently sized fingers can be readily accommodated.

In one embodiment of the present invention the distance between laser 14 and condensing lens 18 is about 5. cm. (2 inches), the distance between the bottom of platen 26 and imaging lens 24 is about 10 cm. (4 inches) and the distance between imaging lens 24 and array 12 is about 2.5 cm. (1 inch). The bracket leg 36a is of sufficient length to permit rotation without contacting the hand of the person whose finger is being scanned.

What I claim is:

1. An improved fingerprint processing apparatus capable of generating a roll fingerprint image, the apparatus of the type having a source of an interrogating light beam, the beam capable of being modulated to provide a reflected light beam having fingerprint information, optical scanning means capable of causing the interrogating light beam to scan a fingerprint object, an array of photoelectric transducers, an imaging lens positioned in the path of the reflected light to provide a fingerprint image at said array, said array being arranged in a pre-determined linear form for receiving the modulated light beam and for converting the fingerprint information carried by said modulated light into a plurality of sets of information signals representing a line by line scan of the fingerprint object, and multi-element electrical scanning means to electronically scan the information signal outputs of the array and to synchronize the electric scan to incremental positions of the optical scanning means, the improvement comprising:

a stationary, cylindrical-segment platen capable of providing a fingerprint object having ridge zones and valley zones, said platen having an upper surface capable of receiving, positioning, and supporting a finger and a lower surface adapted to receive an interrogating light beam, said upper surface having first anti-reflective means for providing said upper surface with image enhancement properties, a finger when positioned on said upper platen surface capable of modulating said interrogating light beam; and means for rotating said light source, said optical scanning means, said array, said lens means and at least one element of said electrical scanning means such that the axis of rotation of said optical scanning means is substantially the same as the axis of the upper surface of said cylindrical-segment platen;

said optical scanning means scanning the circumference of said platen such that the angle of incidence of said interrogating light beam on the finger at the curved back surface of said platen is constant;

said electrical scan being along the axis of said cylindrical-segment platen to thus generate a roll fingerprint image.

2. The improvement of claim 1 wherein said means for rotary movement is capable of moving said optical scanning means through an arc of about 150°.

3. The improvement of claim 1 and additionally comprising second anti-reflective means associated with said lower platen surface for providing said lower platen surface with anti-reflective properties.

4. The improvement of claim 3 wherein said first and said second anti-reflective means each comprise a thin anti-reflective coating on said upper and lower platen surfaces respectively.

5. The improvement of claim 1 and additionally comprising a platen holder for holding the cylindrical-segment platen in its stationary position.

6. The improvement of claim 1 and additionally comprising a bracket connected to said means for rotary movement, said bracket including a platform segment upon which said array and said light source are mounted.

7. The improvement of claim 1 wherein there are a plurality of cylindrical-segment platens each of said cylindrical-segment platens being sized such as to accommodate differently sized fingers.

8. The improvement of claim 1 and having two spherical condensing lenses for shaping said interrogating light beam such that it is a substantially collimated light beam capable of scanning the length of a finger positioned on the platen.

9. The improvement of claim 1 wherein said platen has a length longer than the length of a finger portion to be scanned.

10. The method of generating a roll fingerprint image comprising the steps of:

placing a finger on a cylindrical-segment platen to provide a fingerprint object having ridge zones and valley zones;

scanning an interrogating light beam across the circumference of said platen such that the angle of incidence of said interrogating light beam on said fingerprint object remains constant;

modulating said interrogating light beam with said fingerprint object to provide a reflected light beam having fingerprint information;

imaging said reflected light beam to provide a fingerprint image;

interrogating said fingerprint image at angular intervals corresponding to a linear separation between successive positions of the rotary light scan; and providing a set of electrical signals representing a value at each of said intervals.

* * * * *